(12) United States Patent
Terry

(10) Patent No.: US 6,931,269 B2
(45) Date of Patent: Aug. 16, 2005

(54) MULTI-DOMAIN MOTION ESTIMATION AND PLETHYSMOGRAPHIC RECOGNITION USING FUZZY NEURAL-NETS

(75) Inventor: Alvin Mark Terry, Longmont, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 0 days.

(21) Appl. No.: 10/927,837

(22) Filed: Aug. 27, 2004

(65) Prior Publication Data

US 2005/0049470 A1 Mar. 3, 2005

Related U.S. Application Data

(60) Provisional application No. 60/498,032, filed on Aug. 27, 2003.

(51) Int. Cl.[7] .............................. A61B 5/00; A61B 5/02
(52) U.S. Cl. ..................... 600/336; 128/925; 600/322; 600/323; 600/500; 600/502
(58) Field of Search .................. 600/310, 322, 600/323, 336, 481, 483, 485, 500, 502; 128/925

(56) References Cited

U.S. PATENT DOCUMENTS

| | | | | |
|---|---|---|---|---|
| 5,533,511 A | * | 7/1996 | Kaspari et al. ............. 600/485 |
| 6,035,223 A | * | 3/2000 | Baker, Jr. .................... 600/323 |
| 6,280,381 B1 | * | 8/2001 | Malin et al. ................ 600/322 |
| 6,512,936 B1 | * | 1/2003 | Monfre et al. .............. 600/322 |
| 6,512,937 B2 | * | 1/2003 | Blank et al. ................ 600/322 |
| 6,697,654 B2 | * | 2/2004 | Lorenz et al. .............. 600/310 |
| 6,788,965 B2 | * | 9/2004 | Ruchti et al. ............... 600/310 |

* cited by examiner

Primary Examiner—Eric F. Winakur
(74) Attorney, Agent, or Firm—Marsh Fischmann & Breyfogle LLP

(57) ABSTRACT

Pulse oximetry is improved through classification of plethysmographic signals by processing the plethysmographic signals using a neural network that receives input coefficients from multiple signal domains including, for example, spectral, bispectral, cepstral and Wavelet filtered signal domains. In one embodiment, a plethysmographic signal obtained from a patient is transformed (240) from a first domain to a plurality of different signal domains (242, 243, 244, 245) to obtain a corresponding plurality of transformed plethysmographic signals. A plurality of sets of coefficients derived from the transformed plethysmographic signals are selected and directed to an input layer (251) of a neural network (250). The plethysmographic signal is classified by an output layer (253) of the neural network (250) that is connected to the input layer (251) by one or more hidden layers (252).

45 Claims, 9 Drawing Sheets

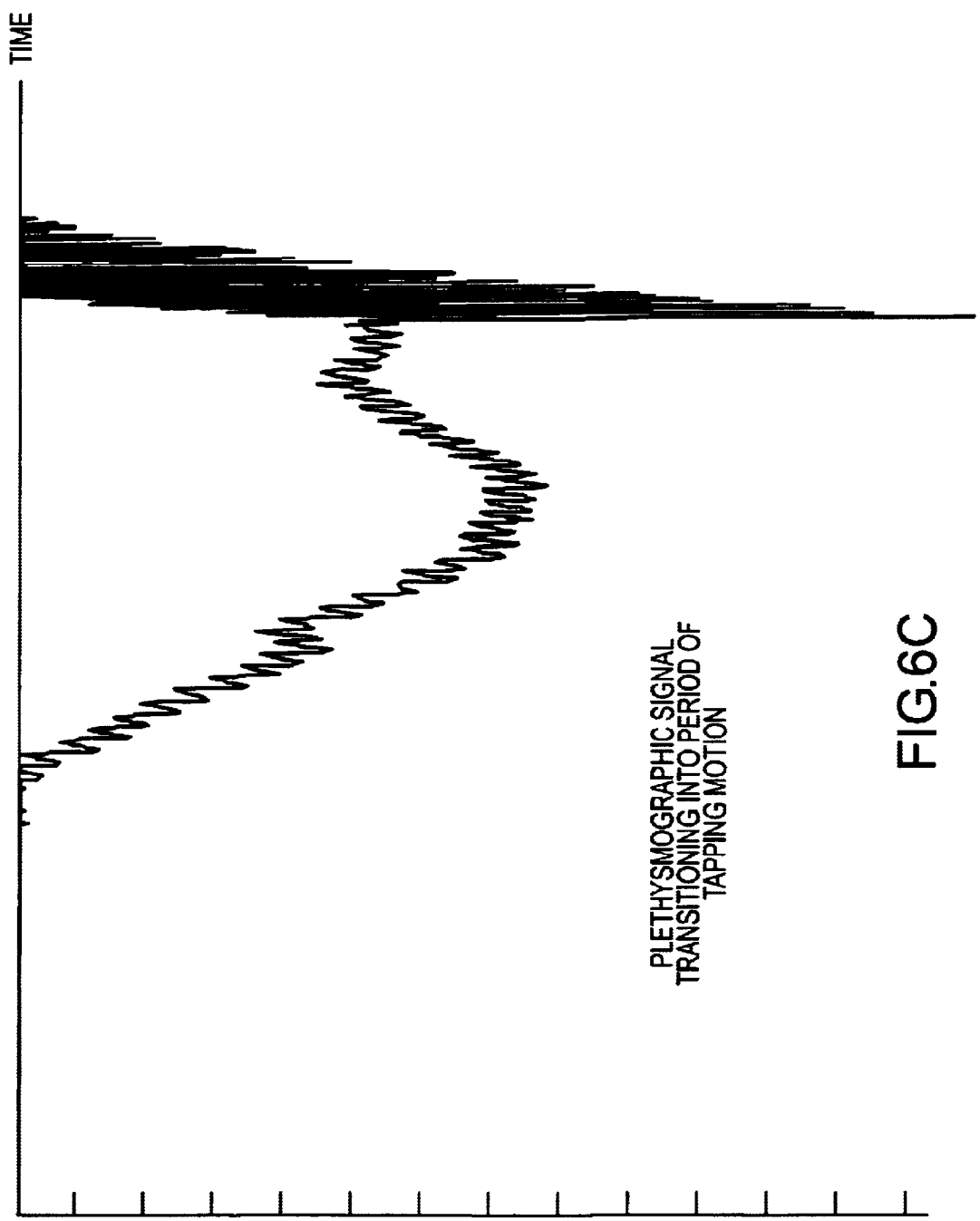

MULTI-DOMAIN MOTION ESTIMATION AND PLETHYSMOGRAPHIC RECOGNITION USING FUZZY NEURAL-NETS

RELATED APPLICATION INFORMATION

This application claims priority from U.S. Provisional Application Ser. No. 60/498,032 entitled "MULTI-DOMAIN MOTION ESTIMATION AND PLETHYSMOGRAPHIC RECOGNITION USING FUZZY NEURAL-NETS" filed on Aug. 27, 2003, the entire disclosure of which is incorporated herein.

FIELD OF THE INVENTION

The present invention relates generally to plethysmographic signal processing, and more particularly to the application of neural net processes to the classification of plethysmographic signals and the estimation of motion therein.

BACKGROUND OF THE INVENTION

Signal attenuation measurements generally involve transmitting a signal towards or through a tissue medium under analysis, detecting the signal transmitted through or reflected by the medium and computing a parameter value for the medium based on attenuation of the signal by the medium. In simultaneous signal attenuation measurement systems, multiple signals are simultaneously transmitted (i.e., two or more signals are transmitted during at least one measurement interval) to the medium and detected in order to obtain information regarding the medium.

Such attenuation measurement systems are used in various applications in various industries. For example, in the medical or health care field, optical (i.e., visible spectrum or other wavelength) signals are utilized to monitor the composition of respiratory and anesthetic gases, and to analyze tissue or a blood sample with regard to oxygen saturation (SpO2 level), analyte values (e.g., related to certain hemoglobins) or other composition related values.

The case of pulse oximetry is illustrative. Some pulse oximeters extract information regarding patient physiological conditions such as the patient's pulse rate and an oxygen saturation level of the patient's blood, or related analyte values, via analysis of plethysmographic signals or waveforms corresponding to different wavelengths of light transmitted through or reflected from the patient's tissue. In particular, pulse oximeters generally include a probe for attaching to a patient's tissue site such as a finger, earlobe, nasal septum, or foot. The probe is used to transmit pulsed optical signals of at least two wavelengths, typically red and infrared, to the patient's tissue site. The different wavelengths of light used are often referred to as the channels of the pulse oximeter (e.g., the red and infrared channels). The optical signals are attenuated by the patient tissue site and subsequently are received by a detector that provides an analog electrical output signal representative of the received optical signals. The attenuated optical signals as received by the detector are often referred to as the transmitted signals. The electrical signal can be processed to obtain plethysmographic signals for each channel and the plethysmographic signals may be analyzed to obtain information regarding patient physiological conditions.

Extraction of patient physiological conditions from the plethysmographic signals can be quite effective using a well positioned sensor and when the patient or subject is resting. However motion artifacts can easily swamp the desired information included in the plethysmographic signals when the patient is moving around and/or performing muscular contractions. Some motion artifacts can severely impair the signals, whereas other types can be filtered out or do not significantly effect the desired information included in the plethysmographic signals. Furthermore, depending upon the severity and type of motion artifacts present in the plethysmographic signals, some techniques for extracting the desired patient physiological conditions may not be appropriate and alternative techniques may need to be employed. Another potential problem that can occur when attempting to make a pulse oximetry system robust to motion artifacts is that heart arrhythmia or rapid pulse variations might possibly be sensed as motion effects and cause motion rejection steps to be applied which may be inappropriate in these cases and could cause false pulse-rate and SpO2 readings.

SUMMARY OF THE INVENTION

Accordingly, the present invention is directed to the use of multiple signal domains in conjunction with neural net processing to achieve pattern classification of different types of motion artifacts and also to classify different patterns of pulse and plethysmographic waveforms that can occur under different physiological conditions. The implementation of a neural-net pattern recognition stage within a pulse oximeter addresses a number of the aforementioned problems thereby achieving an improved instrument.

In accordance with the present invention, motion classification is performed using features extracted from the time, spectral (e.g. power spectral), bispectral and cepstral domains. These features and the spectral (e.g. power spectral), bispectral, and cepstral coefficients are input to a neural network (also referred to herein as a neural-net) to perform recognition of plethysmographic waveforms, and the type of motion or combination of pulsatile waveform and motion artifacts. Another form of information that can be used is coefficients derived from a Wavelet filter bank.

The information from the different sources described above is weighted and processed via a neural-net and the output classification of the neural-net is then used to help with filtering out of motion artifacts and in the decision to use selective portions of high-pass frequency information (AC) in SpO2 calculations. The classification from the neural-net is used to determine the existence and severity and type of motion artifact. The motion classification can be used to improve the signal extraction in noisy conditions, and to aid in selection of the most appropriate signal extraction method. Further the neural-net classifier can be used to determine the type of plethysmographic signal, such as normal adult, infant, or that produced from different types of heart conditions. Identification of the signal type will aid in measurement and in extraction of the signal from noise.

One aspect of the invention is in describing the different types of physiological and noise conditions for which plethysmographic waveforms are collected for training the neural-net classifier. In order to improve the robustness of the classifier the inputs to the neural-net during training are subjected to 'fuzzification' wherein input values are slightly perturbed and reordered. This process increases the size of the training set and also has the effect of making the neural-net less rigid in its ability to classify patterns. The training of the neural-net can also be enhanced by use of a fuzzy logic controller which is used to adjust learning parameters and to speed up convergence during back-propagation learning.

Another aspect of the invention is that the neural-net is trained to respond to different respiration activities—both rate and depth. Pertinent information from spectral coefficients, and Wavelet transforms on the different input wavelengths (typically red and infrared, but also additional wavelengths which may be used) are presented to the neural-net. Optionally derived SpO2 estimates can also be presented. All this information can be used to obtain further more robust SpO2 estimates. Thus the neural-net provides a variety of information which can be used to classify respiration conditions.

According to another aspect of the invention, a pulse oximeter includes a first optical signal source that is operable to emit an optical signal characterized by a first wavelength (e.g., red) and a second optical signal source that is operable to emit an optical signal characterized by a second wavelength (e.g., infrared) different than the first wavelength. A detector operable to receive the first and second optical signals after they are attenuated by a patient tissue site provides a detector output signal representative of the attenuated first and second optical signals. A processor is enabled to obtain first and second time domain plethysmographic signals from the detector output signal. The processor also classifies one or more of the first and second time domain plethysmographic signals using a neural network. The neural network receives input coefficients derived from one or more transforms of the first and/or second time domain plethysmographic signals. The transforms may, for example, include spectral (e.g., power spectral), bispectral, cepstral, and Wavelet filter bank transforms.

According to a further aspect of the present invention, a method of processing a plethysmographic signal obtained from a patient in a first signal domain (e.g., time) includes transforming the plethysmographic signal from the first domain to a plurality of signal domains different from the first domain. The different signal domains may, for example, include spectral (e.g., power spectral), bispectral, cepstral, and Wavelet filtered domains. Transformation of the first domain plethysmographic signal results in a plurality of transformed plethysmographic signals with each transformed plethysmographic signal being in one of the different signal domains. A plurality of sets of coefficients are selected, with each set of coefficients being derived from a corresponding one of the transformed plethysmographic signals. The sets of coefficients are input to a neural network, and the plethysmographic signal is classified based on an output from the neural network.

According to yet another aspect of the present invention, a method of training a neural network to classify a plethysmographic signal obtained from a patient includes selecting a plurality of first domain plethysmographic signal data sets associated with a plurality of different types of predetermined signal conditions from a database of plethysmographic signal data sets. The first domain plethysmographic signal data sets are transformed to other signal domains different than the first domain to obtain a corresponding plurality of transformed plethysmographic signal data sets. In this regard, the first domain may, for example, be the time domain and the other signal domains include, for example, spectral (e.g., power spectral), bispectral, cepstral, and Wavelet filtered domains. A plurality of sets of coefficients are extracted from the transformed plethysmographic signal data sets, with each set of coefficients being extracted from a corresponding one of the transformed plethysmographic signal data sets. The sets of extracted coefficients are used as inputs to the neural network, and weighting values associated with connections between neurons in the neural network are adjusted in accordance with a learning procedure. The learning procedure may, for example, be a backpropagation learning procedure or a simulated annealing learning procedure. Where desired, the backpropagation learning procedure may be implemented with fuzzy logic control.

According to one more aspect of the present invention, a method of providing information relating to a physiological condition of a patient based on at least one plethysmographic signal obtained from the patient in a first signal domain (e.g., time) includes transforming the plethysmographic signal from the first domain to a plurality of signal domains different from the first domain. The different signal domains may, for example, include spectral (e.g., power spectral), bispectral, cepstral, and Wavelet filtered domains. Transformation of the first domain plethysmographic signal results in a plurality of transformed plethysmographic signals with each transformed plethysmographic signal being in one of the different signal domains. The plethysmographic signal is classified based on an output from a neural network. The output of the neural network is based on input coefficients derived from one or more of the transformed plethysmographic signals. Based on the classification, a technique for determining the physiological condition of the patient is selected. The physiological condition of the patient may, for example, comprise a pulse rate. Where at least two plethysmographic signals corresponding to different optical wavelengths are transformed and classified, the physiological condition of the patient may, for example, comprise an SpO2 value or a respiration index. Where the physiological condition of the patient comprises a respiration index, the plethysmographic signals are preferably transformed using at least a Wavelet filter bank transform.

These and other aspects and advantages of the present invention will be apparent upon review of the following Detailed Description when taken in conjunction with the accompanying figures.

DESCRIPTION OF THE DRAWINGS

For a more complete understanding of the present invention and further advantages thereof, reference is now made to the following Detailed Description, taken in conjunction with the drawings, in which:

FIGS. 6A–6D are plots showing exemplary plethysmographic signal conditions that may be included within a database of plethysmographic training sets.

DETAILED DESCRIPTION

Figure 1:
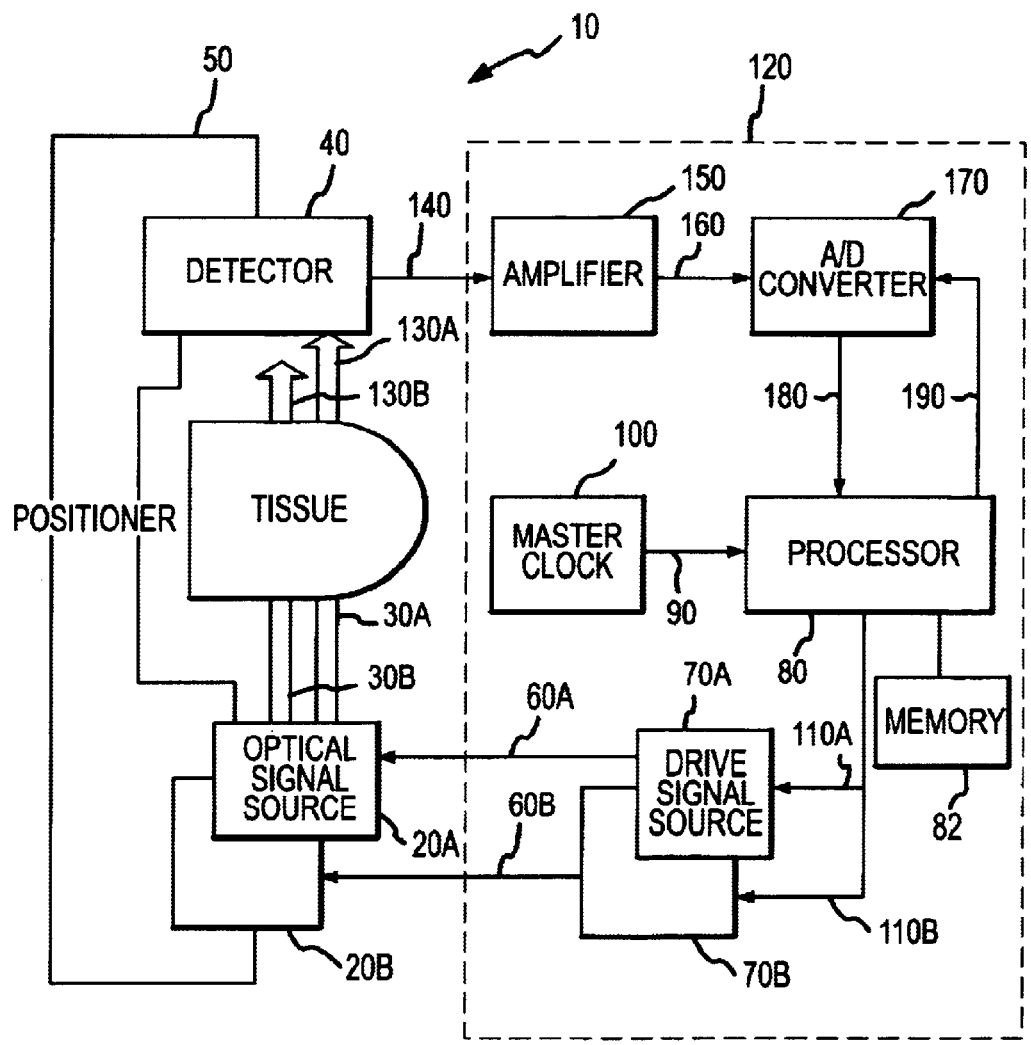
FIG. 1 is a block diagram of one embodiment of a pulse oximeter employing multi-domain motion estimation and plethysmographic signal recognition using fuzzy neural-nets in accordance with the present invention.

Referring now to FIG. 1, there is shown a block diagram of one embodiment of a pulse oximeter 10 in which multi-domain motion estimation and plethysmographic signal recognition using fuzzy neural-nets may be implemented. The pulse oximeter 10 is configured for use in determining the pulse rate of a patient as well as one or more blood analyte levels in the patient, such as an SPO2 level. It should be appreciated that multi-domain motion estimation and plethysmographic signal recognition using fuzzy neural-nets in accordance with the present invention may be implemented in pulse oximeters that are configured differently from the pulse oximeter depicted in FIG. 1 as well as in other environments wherein plethysmographic signals are processed in order to obtain desired information relating to patient physiological conditions from the plethysmographic signals.

The pulse oximeter 10 includes a pair of optical signal sources 20a, 20b for emitting a corresponding pair of light signals 30a, 30b centered at different predetermined center wavelengths $\lambda_1$, $\lambda_2$ through a suitable tissue site of a patient and on to a detector 40 (e.g., a photo-sensitive diode). The optical signal sources 20a, 20b and detector 40 may be included in a positioning device 50, or probe, to facilitate alignment of the light signals 30a, 30b with the detector 40. For example, the positioning device 50 may be of clip-type or flexible strip configuration adapted for selective attachment to a suitable patient tissue site (e.g., a finger, an ear lobe, a foot, or the nose of the patient). The center wavelengths $\lambda_1$, $\lambda_2$ required depend upon the blood analyte level to be determined. For example, in order to determine an SPO2 level, $\lambda_1$ may be in the Red wavelength range and $\lambda_2$ may be in the infrared wavelength range. It should be appreciated that the pulse oximeter 10 may be readily implemented with more optical signal sources (e.g., four) depending upon the number of different blood analyte levels to be measured.

The optical signal sources 20a, 20b are activated by a corresponding plurality of drive signals 60a, 60b to emit the light signals 30a, 30b. The drive signals 60a, 60b are supplied to the optical signal sources 20a, 20b by a corresponding plurality of drive signal sources 70a, 70b. The drive signal sources 70a, 70b may be connected with a digital processor 80, which is driven with a clock signal 90 from a master clock 100. The digital processor 80 may be programmed to define modulation waveforms, or drive patterns, for each of the optical signal sources 20a, 20b. In this regard, there may be a separate memory device 82 interfaced with the digital processor 80 (or the memory device 82 may be incorporated in the processor 80) on which various software instructions executable by the processor 80 are stored. More particularly, the digital processor 80 may provide separate digital trigger signals 110a, 110b to the drive signal sources 70a–d, which in turn generate the drive signals 60a, 60b. In this regard, the digital trigger signals 110a, 10b may be configured to provide for multiplexing of the drive signals 60a, 60b, and in turn the light signals 30a, 30b, in accordance with a multiplexing scheme (e.g., time division, frequency division, or code division multiplexing).

The drive signal sources 70a, 70b, processor 80, memory device 82 and clock 100 may all be housed in a monitor unit 120. While the illustrated embodiment shows the optical signal sources 20a, 20b physically interconnected with the positioning device 50 (e.g., mounted within the positioning device 50 or mounted within a connector end of a cable that is selectively connectable with the positioning device 50), it should be appreciated that the optical signal sources 20a, 20b may also be disposed within the monitor unit 120. In the latter case, the light signals 30a, 30b emitted from the optical signal sources 20a, 20b may be directed from the monitor unit 120 via one or more optical fibers to the positioning device 50 for transmission through the tissue site. Furthermore, the drive signal sources 70a, 70b may comprise a single drive signal generator unit that supplies each of the drive signals 60a, 60b to the optical signal sources 20a, 20b.

Transmitted light signals 130a, 130b (i.e., the portions of light signals 30a, 30b exiting the tissue) are detected by the detector 40. The detector 40 detects the intensities of the transmitted signals 130a, 130b and outputs a current signal 140 wherein the current level is indicative of the intensities of the transmitted signals 130a, 130b. As may be appreciated, the current signal 140 output by the detector 40 comprises a multiplexed signal in the sense that it is a composite signal including information about the intensity of each of the transmitted signals 130a, 130b. Depending upon the nature of the drive signals 60a, 60b, the current signal 140 may, for example, be time division multiplexed, wavelength division multiplexed, or code division multiplexed.

The current signal 140 is directed to an amplifier 150, which may be housed in the monitor unit 120 as is shown. As an alternative, the amplifier 150 may instead be included in a probe/cable unit that is selectively connectable with the monitor unit 120. The amplifier 150 converts the current signal 140 to a voltage signal 160 wherein a voltage level is indicative of the intensities of the transmitted signals 130a, 130b. The amplifier 150 may also be configured to filter the current signal 140 from the detector 40 to reduce noise and aliasing. By way of example, the amplifier 150 may include a bandpass filter to attenuate signal components outside of a predetermined frequency range encompassing modulation frequencies of the drive signals 60a, 60b.

Since the current signal 140 output by the detector 40 is a multiplexed signal, the voltage signal 160 is also a multiplexed signal, and thus, the voltage signal 160 must be demultiplexed in order to obtain signal portions corresponding with the intensities of the transmitted light signals 130a, 130b. In this regard, the digital processor 80 may be provided with demodulation software for demultiplexing the voltage signal 160. In order for the digital processor 80 to demodulate the voltage signal 160, it must first be converted from analog to digital. Conversion of the analog voltage signal 160 is accomplished with an analog-to-digital (A/D) converter 170, which may also be included in the monitor unit 120. The A/D converter 170 receives the analog voltage signal 160 from the amplifier 150, samples the voltage signal 160, and converts the samples into a series of digital words 180 (e.g., eight, sixteen or thirty-two bit words), wherein each digital word is representative of the level of the voltage signal 160 (and hence the intensities of the transmitted light signals 130a, 130b) at a particular sample instance. In this regard, the A/D converter 170 should provide for sampling of the voltage signal 160 at a rate sufficient to provide for accurate tracking of the shape of the various signal portions comprising the analog voltage signal 160 being converted. For example, the A/D converter 170 may provide for a sampling frequency at least twice the frequency of the highest frequency drive signal 60a, 60b, and typically at an even greater sampling rate in order to more accurately represent the analog voltage signal.

The series of digital words 180 is provided by the A/D converter 170 to the processor 80 to be demultiplexed. More particularly, the processor 80 may periodically send an interrupt signal 190 (e.g., once per every eight, sixteen or thirty-two clock cycles) to the A/D converter 170 that causes the A/D converter 170 to transmit one digital word 180 to the processor 80. The demodulation software may then demultiplex the series of digital words 180 in accordance with an appropriate method (e.g., time, wavelength, or code) to obtain digital signal portions indicative of the intensities of each of the transmitted light signals 130a, 130b. In this regard, the demultiplexed digital signal portions comprise time domain plethysmographic signals corresponding to the center wavelengths $\lambda_1$, $\lambda_2$ (e.g., red and infrared) of the optical signal sources 20a, 20b. The red and infrared time domain plethysmographic signals may then be processed by the processor 80 to obtain desired patient physiological condition related information therefrom such as the patient's pulse rate and SPO2 level.

Figure 2:
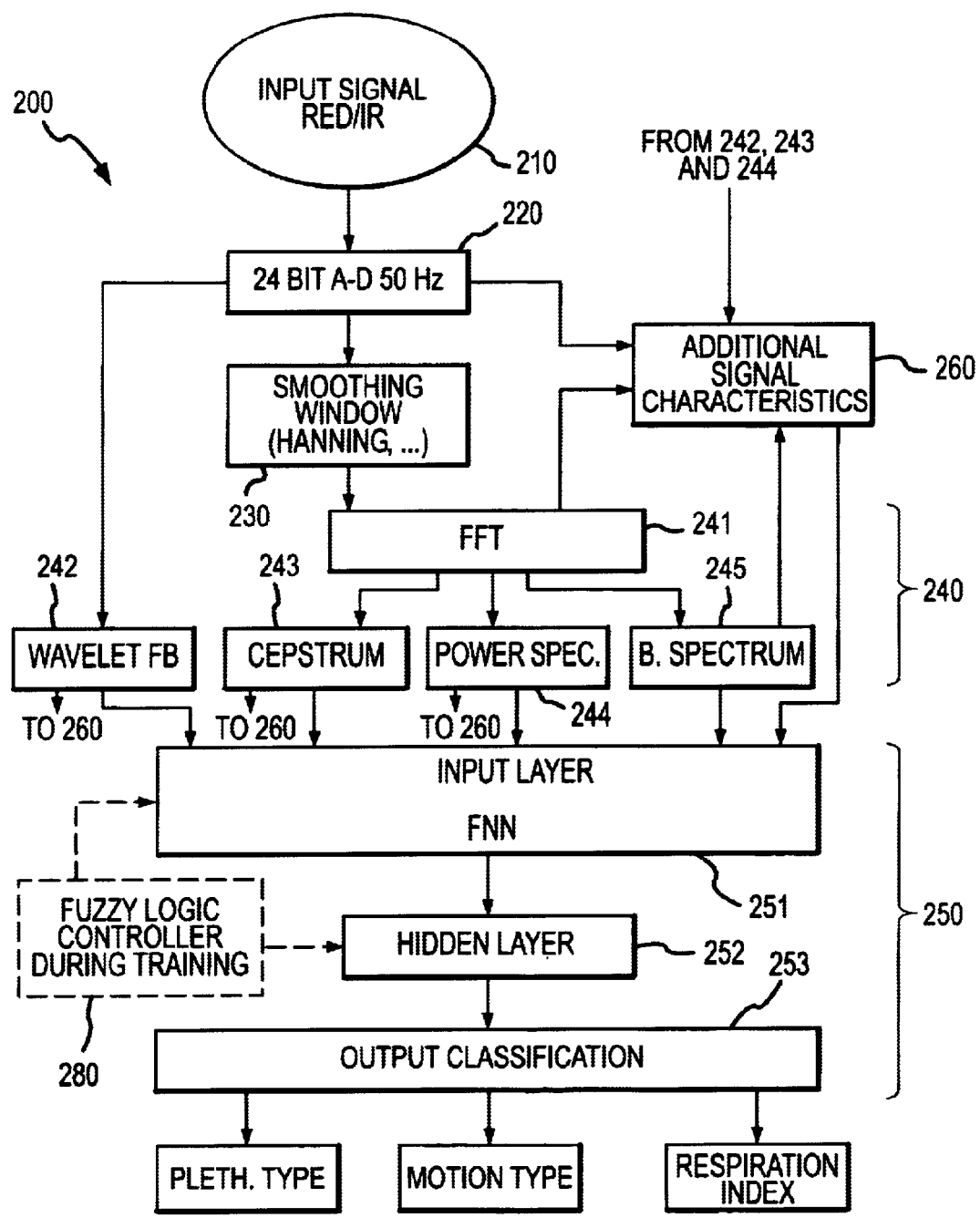
FIG. 2 is a block diagram showing one embodiment of a method of implementing multi-domain motion estimation and plethysmographic signal recognition using fuzzy neural-nets in accordance with the present invention.

Referring now to FIG. 2, there is shown one embodiment of a fuzzy neural-net multi-domain motion estimation and plethysmographic recognition signal processing method (200) that may be implemented on a pulse oximeter 10 such as illustrated in FIG. 1. In this regard, where the processor 80 comprises a general purpose microprocessor or the like, the signal processing method (200) may, for example, be implemented in computer software instructions executable by the processor 80. In other embodiments, the signal processing method (200) may be implemented in hardware, such as where the processor 80 comprises a field programmable gate array (FPGA) or an application specific integrated circuit (ASIC) or the like.

Figure 4:
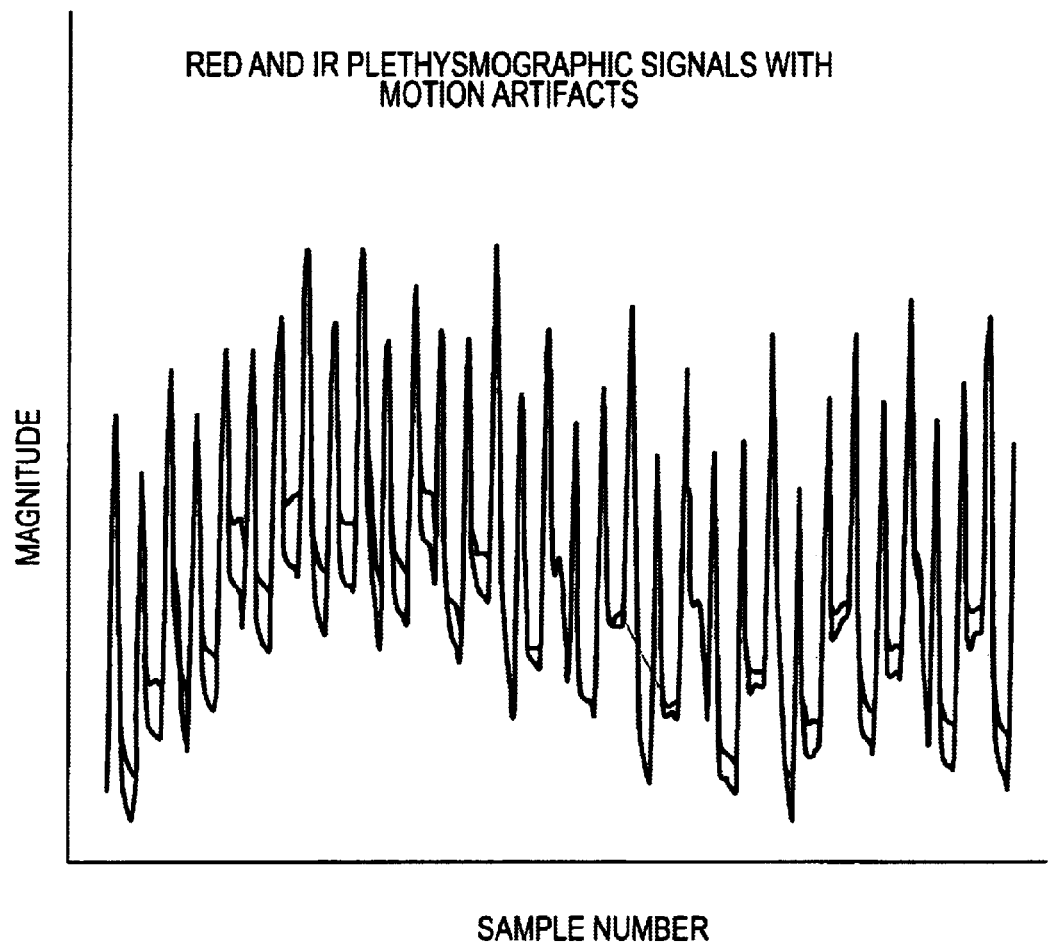
FIG. 4 is a plot of exemplary red and infrared plethysmographic signals that include motion artifacts.

The signal processing method (200) starts with obtaining (210) two continuous time domain plethysmographic signals such as red and infrared plethysmographic signals. The red and infrared plethysmographic signals are digitized (220) by sampling the signals at a suitable frequency (e.g., at least about 50 Hz). Typical red and infrared time domain plethysmographic signals that have been sampled at 50 Hz are shown in FIG. 4. The signals depicted in FIG. 4 include motion artifacts. While the method (200) is illustrated with two input plethysmographic signals, in other embodiments, the signal processing method (200) may be configured for processing only one plethysmographic signal or processing more than two plethysmographic signals.

The digitized time domain red and infrared plethysmographic signals are directed to a smoothing module (230) wherein they are smoothed via a suitable smoothing window (e.g. Hanning, Hamming, or Kaiser). Smoothing the digitized plethysmographic signals achieves improved frequency estimation and prevents frequency spreading from discontinuities that would be seen with a rectangular time window. However, smoothing may not be advantageous in all instances and thus may not be incorporated in other embodiments of the method (200).

Thereafter, the red and infrared plethysmographic signals are transformed (240) from the time domain to other suitable signal domains. Such signal domains include the cepstral domain, a Wavelet filtered domain, and various spectral domains. In this regard, nth order cumulant spectral domains such as, for example, the power spectrum (n=2), the bispectrum (n=3), and the trispectrum (n=4) are generally of interest, with the power spectrum and the bispectrum being particularly useful. In this regard, the bispectrum can be used to obtain a coherence index that is useful to characterize non-linearities in time series via phase relations of harmonic components. In practical terms, this means that the bispectrum has advantages for use in recognition of the pulse signature among various noise components that may be present in the time domain plethysmographic signals.

Transformation (240) of the time domain red and infrared plethysmographic signals may be accomplished in a number of manners. As illustrated in FIG. 2, the digitized and smoothed time domain plethysmographic signals may first be processed in parallel via a complex FFT processing module (241). The complex FFT processing module (241) outputs spectral domain red and infrared plethysmographic signals. If desired, the results of the FFT calculation may be scaled to help prevent floating point errors in subsequent computations. The output from the complex FFT processing module (241) is then directed to a cepstrum processing module (243), and various nth-order cumulant spectral domain processing modules, including, in this embodiment, a power spectrum processing module (244) and a bispectrum processing module (246).

As part of the transformation (240), the digitized time domain red and infrared plethysmographic signals are also directed to a Wavelet filter bank processing module (242). The Wavelet filter bank processing module (242) applies a Wavelet transform to the time domain plethysmographic signals. The Wavelet filter bank processing module (242) outputs sets of coefficients corresponding to each of the input plethysmographic signals (the red and infrared Wavelet filtered domain coefficient sets). Each of Wavelet filtered domain coefficient sets are directed from the Wavelet filter bank processing module (242) to an input layer (251) of a neural network processing module (250).

The cepstrum processing module (243) transforms the spectral domain plethysmographic signals output by the complex FFT processing module (241) to cepstral domain plethysmographic signals. One manner of obtaining the cepstral domain plethysmographic signals is to first compute logarithmic scaled power spectra from the spectral domain plethysmographic signals and then apply a second stage complex FFT. In this regard, more detail concerning cepstral domain processing of plethysmographic signals is provided in U.S. Pat. No. 6,650,918 entitled "CEPSTRAL DOMAIN PULSE OXIMETRY", the entire disclosure of which is hereby incorporated by reference herein. If desired, the results of the FFT calculation may be scaled to help prevent floating point errors in subsequent computations. The cepstrum processing module (243) outputs sets of coefficients corresponding to each of the input plethysmographic signals (the red and infrared cepstral domain coefficient sets). Each of the cepstral domain coefficient sets are directed from the cepstrum processing module (243) to the input layer (251) of the neural network processing module (250).

The power spectrum processing module (244) computes red and infrared power spectrums from the spectral domain plethysmographic signals output by the complex FFT processing module (241). In this regard, the red and infrared power spectrums may be computed by squaring and summing the appropriate real and imaginary frequency components obtained by the FFT. The power spectrum processing module (243) outputs sets of coefficients corresponding to each of the input plethysmographic signals (the red and infrared power spectral domain coefficient sets). Each of power spectral domain coefficient sets are directed from the power spectrum processing module (243) to the input layer (251) of the neural network processing module (250).

The bispectrum processing module (244) computes red and infrared bispectrums from the spectral domain plethysmographic signals output by the complex FFT processing module (241). In this regard, for a Fourier transform F(ω), the red and infrared bispectrums are defined in accordance with the following expression:

$$B(\omega_1,\omega_2)=E[F(\omega_1)F(\omega_2)\overline{F(\omega_1+\omega_2)}]$$

where $\omega_1$ and $\omega_2$ are the frequencies present in the spectrums. The bispectrum processing module (244) outputs sets of coefficients corresponding to each of the input plethysmographic signals (the red and infrared bispectral domain coefficient sets). Each of bispectral domain coefficient sets are directed from the bispectrum processing module (244) to the input layer (251) of the neural network processing module (250).

It should be noted that in other embodiments, transformation (240) of the digitized time domain plethysmographic signals may not involve all of the domains shown in FIG. 2. For example, only one of the cepstral, power spectral, bispectral, or Wavelet filtered domains may be employed. Or, a different combination of such domains (e.g., cepstral and power spectral, cepstral and bispectral, etc.) may be employed. Furthermore, in other embodiments transformation (240) may only involve application of a Wavelet filter to the digitized time domain plethysmographic signals without employing the complex FFT processing module (241) to derive only Wavelet filtered time domain coefficients.

The various sets of red and infrared Wavelet filtered domain, cepstral domain, power spectral domain, and bispectral domain coefficients may be concatenated in vector form for presentation to the neural network input stage. The assembled vector basically represents the information present to the time epoch of the smoothing window. Each successive assembled vector or frame represents different successive time samples of the input signal, in sync with the smoothing window time shift increment (typically half the duration of the smoothing window). Each red and infrared vector is associated with a single frame of sample instances in the digitized time domain plethysmographic signals. In this regard, processing of the red and infrared plethysmographic signals in accordance with the method (200) depicted in FIG. 2 is preferably undertaken each time a number m of new sample instances is/are received upon digitizing (220) the input plethysmographic signals. In this regard, m may be one, two, or more sample instances, and m may be predetermined or may vary depending upon factors such as classification of the signal in accordance with the method (200). Thus, each time m sample instances is/are received, a new frame is established.

Each frame may correspond with a window of sample instances. In this regard, the window length may be fixed. For example, the current sample instance and n past sample instances (n being a predetermined number) may be used in performing the various calculations involved in the transformation (240) of the plethysmographic signals into the various signal domains. The predetermined number n may, for example, be determined empirically based on tests conducted using known plethysmographic data sets or it may be established during training of the neural network processing module (250). The window length may also vary. For example, the current sample instance and a varying number of past sample instances may be used in performing the various calculations involved in the transformation (240) of the plethysmographic signals into the various signal domains. The number of past sample instances included in the varying length window may, for example, be varied depending upon factors such as classification of the signal in accordance with the method (200). As may be appreciated, current calculations will not be influenced by older sample instances that are discarded once outside the window length.

Alternatively, each frame may be recursive. In this regard, the current sample instance and all past sample instances are included in each successive frame. As may be appreciated, current calculations will be influenced by older sample instances since no sample instances are discarded when the frames are of the recursive type. However, the influence of older sample instances on current calculations can be reduced, if desired, by weighting older sample instances less than current sample instances.

Each time a frame is established, the various sets or vectors of red and infrared Wavelet filtered domain, cepstral domain, power spectral domain, and bispectral domain coefficients associated with each respective frame are directed to the input layer (251) of the neural network processing module (250). In addition to the various sets of coefficients, the input layer (251) may also receive additional inputs from an additional signal characteristics processing module (260). The additional signal characteristics may be derived by the additional signal characteristics processing module (260) from one or more of the red and infrared digitized signals, spectral domain signals, cepstral domain signals, power spectral signals, and bispectral signals. Such additional signal characteristics include: (1) an RMS energy measure; (2) a spikiness measure; (3) a spectral jitter measure; (4) a spectral shimmer measure; (5) a spectral smear measure; (6) cepstral peak jitter measure; and (7) a cepstral peak position measure.

The input layer (251) assembles the various coefficients and additional signal characteristics, if any, received thereby and directs such inputs (as appropriately weighted) to one or more hidden layers (252) of the neural network (250). The hidden layer(s) (252) receive the appropriately weighted input coefficients and additional signal characteristics, if any, and direct such values (as appropriately weighted) therefrom to an output layer (253) of the neural network (250). Preferably, inputs from at least three data frames are processed simultaneously by the neural network (250) to classify the red and infrared plethysmographic signals by plethysmographic signal type (271) and motion artifact type (272), as well as to generate a respiration index (273) (e.g., depth and rate).

Once the plethysmographic signals (or frames thereof) are classified, the processor 80 of the pulse oximeter 10 may utilize the information in various manners. For example, based on the plethysmographic signal type and motion type, the processor 80 may undertake different filtering of the plethysmographic signals before deriving physiological conditions from the signals. For example, for a tapping motion the processor 80 may choose to examine the cepstral transform to extract the signal pulse component. For a severe clenching motion the processor 80 may decide to use DC tracking to determine SpO2 and choose not to attempt to extract the pulse frequency. If the net output classification indicated a highly irregular plethysmographic signal type but little motion artifact then the processor 80 might extract pulse rate frequency and SpO2 values from the time domain. By way of further example, based on the plethysmographic type and motion type, the processor 80 may choose to adjust how patient physiological conditions are derived from the plethysmographic signals. In this regard, the neural network classifier can be trained on abnormal signals (e.g., extreme arrhythmia's and different heart conditions) so that it will be able to alert medical personnel to occurrence of unusual waveforms possibly due to the onset of a critical physiological condition.

Figure 3:
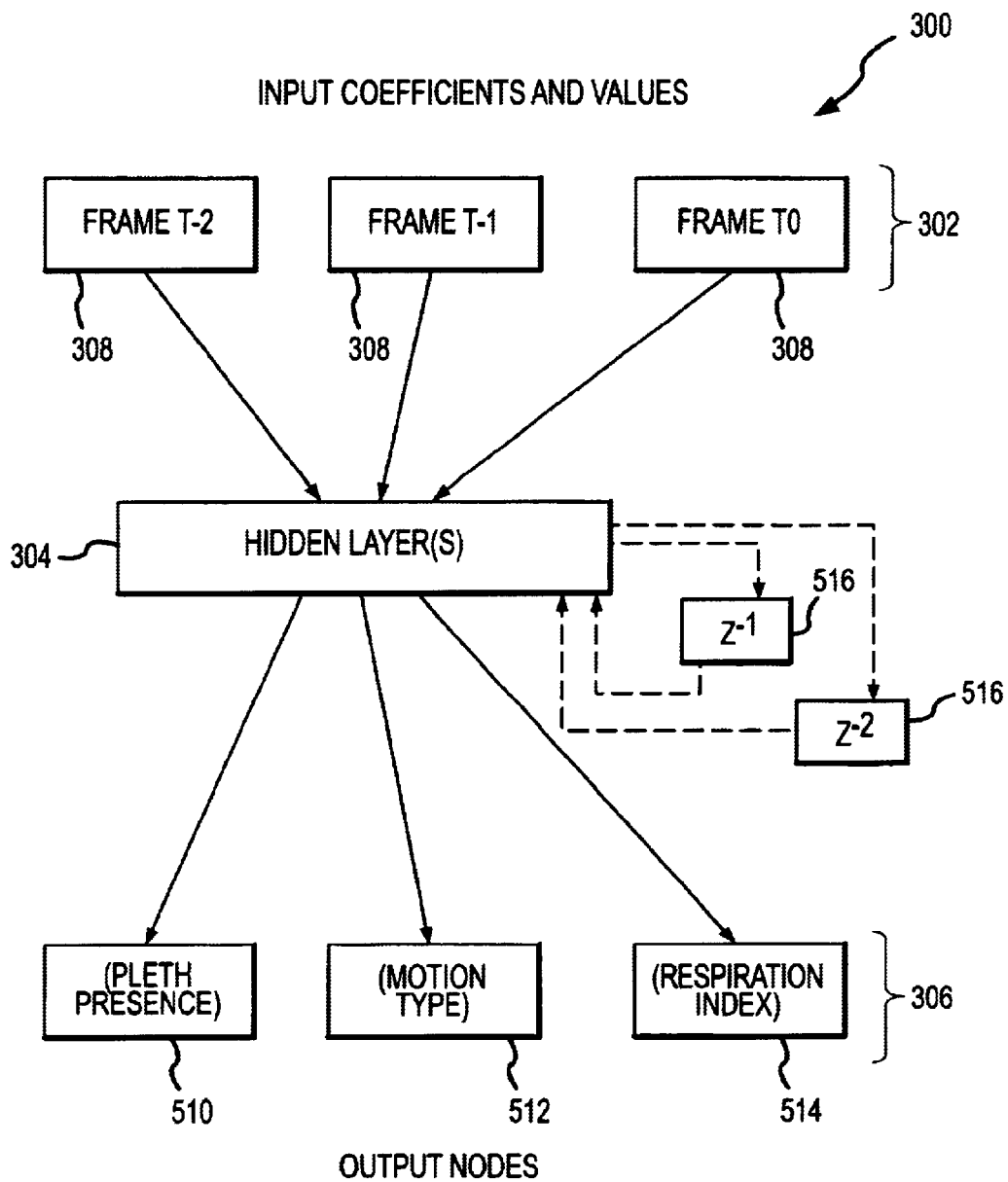
FIG. 3 is a schematic diagram illustrating one embodiment of a neural network architecture that may be employed in accordance with the present invention.

Referring now to FIG. 3, there is shown a schematic representation of one embodiment of a neural network 300 architecture that may be employed for plethysmographic recognition, respiration activity and motion estimation in accordance with the method (200) illustrated in FIG. 2. The neural network 300 includes an input layer 302, one or more hidden layers 304, and an output classification layer 306. The input layer 302 receives input values in the form one or more frames 308 of input values produced at different times from the current frame t0 backwards to frame t−n, where n is an integer. As depicted, in one embodiment there are three frames (t0, t−1, t−2). The time interval between frames 308 may be linear, as depicted, or it may be non-linear. Each frame 308 may be made up of input values from a variety of signal transforms (e.g., cepstral, bispectral, Wavelet, power spectral) as well as additional signal characteristics, if any.

Each value in the frames 308 activates a separate node (also referred to herein as neuron) in the neural network 300 input layer 302. Each node in the input layer 302 activates each node in the first hidden layer 304 interconnected thereto. There may be one or more hidden layers 304. Each node in the last hidden layer 304 activates each node in the output classification layer 306 interconnected thereto. The output classification layer 306 includes a number of output nodes. The total number of output nodes typically corresponds to the number of different types of classification required. In this regard, the output nodes may generally be classified as being plethysmographic type output nodes 310 or motion type output nodes 312.

The output nodes provide indications as to the presence of the particular type of plethysmographic signal or motion in the red and infrared plethysmographic signals by firing at various levels. A level approaching a specified high value (e.g., 1) indicates a strong presence of the particular type of plethysmographic signal or motion with which the node is associated and a level approaching a specified low value (e.g., 0) indicates a weak presence of the particular type of plethysmographic signal or motion with which the node is associated. Thus, the red and infrared plethysmographic signals are classified by the various levels of the plethysmographic type and motion type output nodes 310, 312.

In addition to the plethysmographic signal type and motion type output nodes 310, 312, there may also be one or more respiration index output nodes 314. For example, there may be a respiration rate output node and a respiration depth output node. The values (e.g., from 0 to 1) of the respiration rate and depth nodes comprise the respiration index of the patient. In order to obtain a respiration index, comparing the Wavelet filter bank coefficients from both the red and infrared input signals over time may offer the neural network 300 the required information necessary to determine respiration activity, since the comparison (which the neural network 300 may do in a number of ways) can provide SpO2 estimates. It is the pattern of such SpO2 estimates over time that provides information to build a respiration index. Similarly allowing the neural network 300 to compare the other spectral transforms from both the red and infrared input signals assists in extracting information that provides SpO2 estimates.

The neural network 300 architecture as described is a feed-forward network, and when there is only a single hidden layer 304, it is a three-layer feed-forward network. Another form of the neural network 300 can be configured by adding unit delay operators 316 at the hidden layer 304. The schematic connections of the unit delay operators 316 are depicted in dashed lines to indicate that they may be optionally included in order to achieve a recursive neural network 300 architecture.

Regardless of the neural network 300 architecture, the neural network 300 should be trained prior to use in order to establish the appropriate weights applied to the various interconnections between the various nodes. One method of training the neural network is the backpropagation algorithm. The backpropagation algorithm may be supervised by a fuzzy logic controller processing module. The fuzzy logic controller is referenced in FIG. 2 as 280 and is depicted in dashed lines to indicate that it may optionally be included when training the neural network 300. The fuzzy logic controller (280) helps speed up the convergence of the backpropagation learning, and in some cases enables convergence to take place, by controlling the learning parameters with a fuzzy rule set. Essentially some heuristics are applied dependent on the change of error (CE—related to error gradient) and the change of CE (CCE—related to second-order error gradient). This has been shown to accelerate learning. The input to the neural network 300 may also be "fuzzified" by slight perturbing and reordering input values. Such a technique can increase the robustness of the neural network 300 to recognize patterns in noise.

Figure 5:
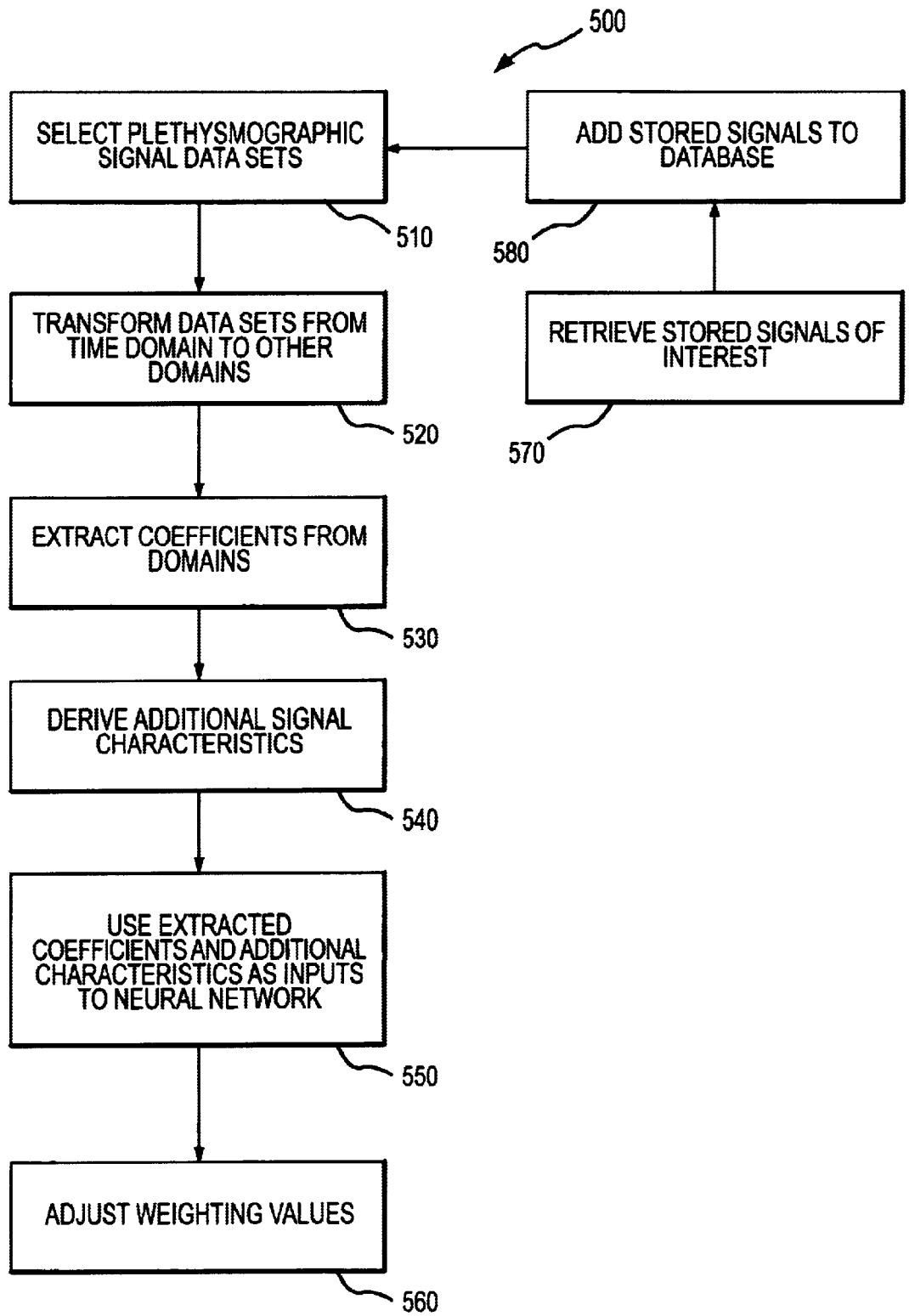
FIG. 5 is a block diagram showing one embodiment of a neural network training method in accordance with the present invention.
Figure 6A:
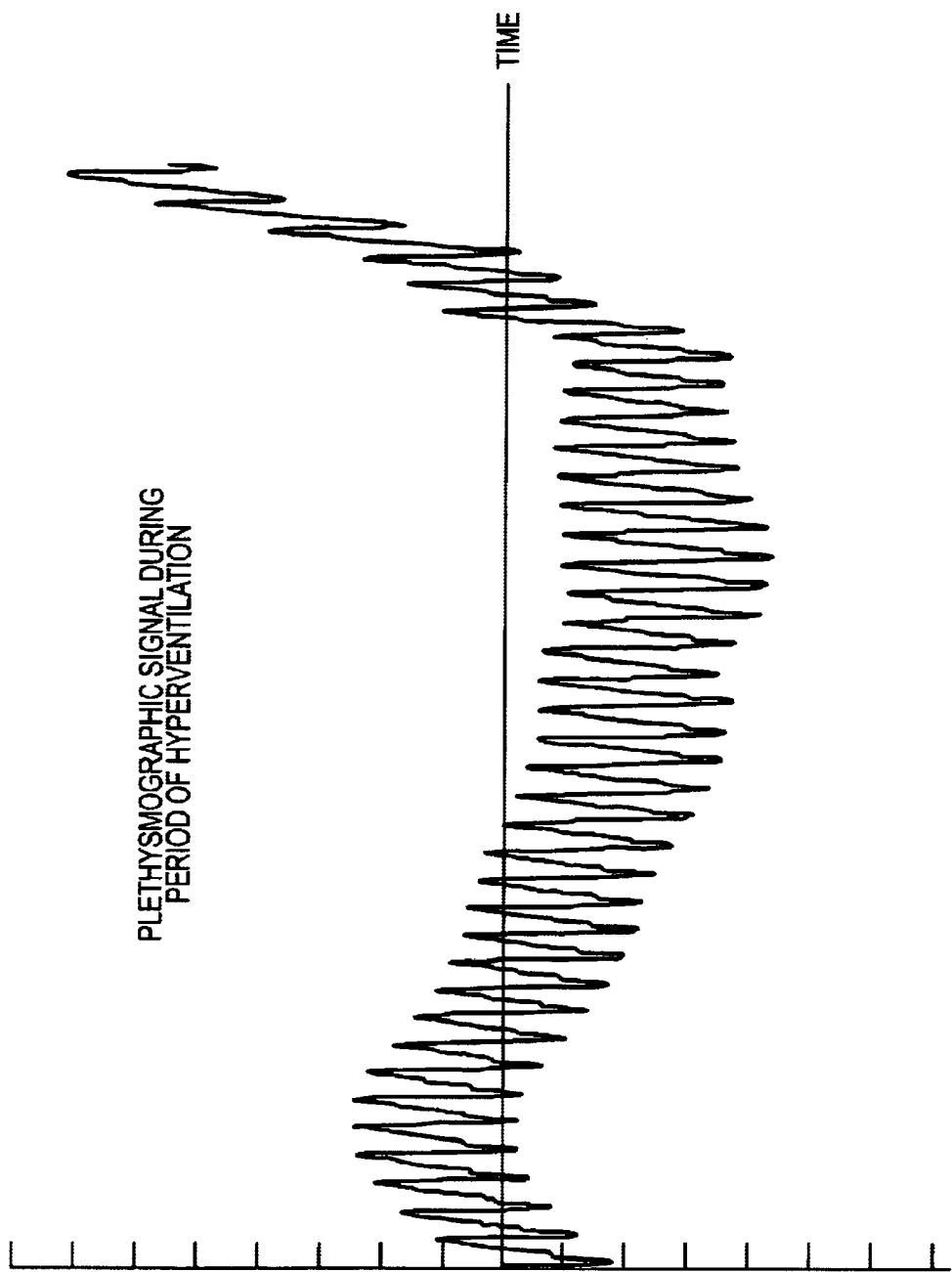
Figure 6B:
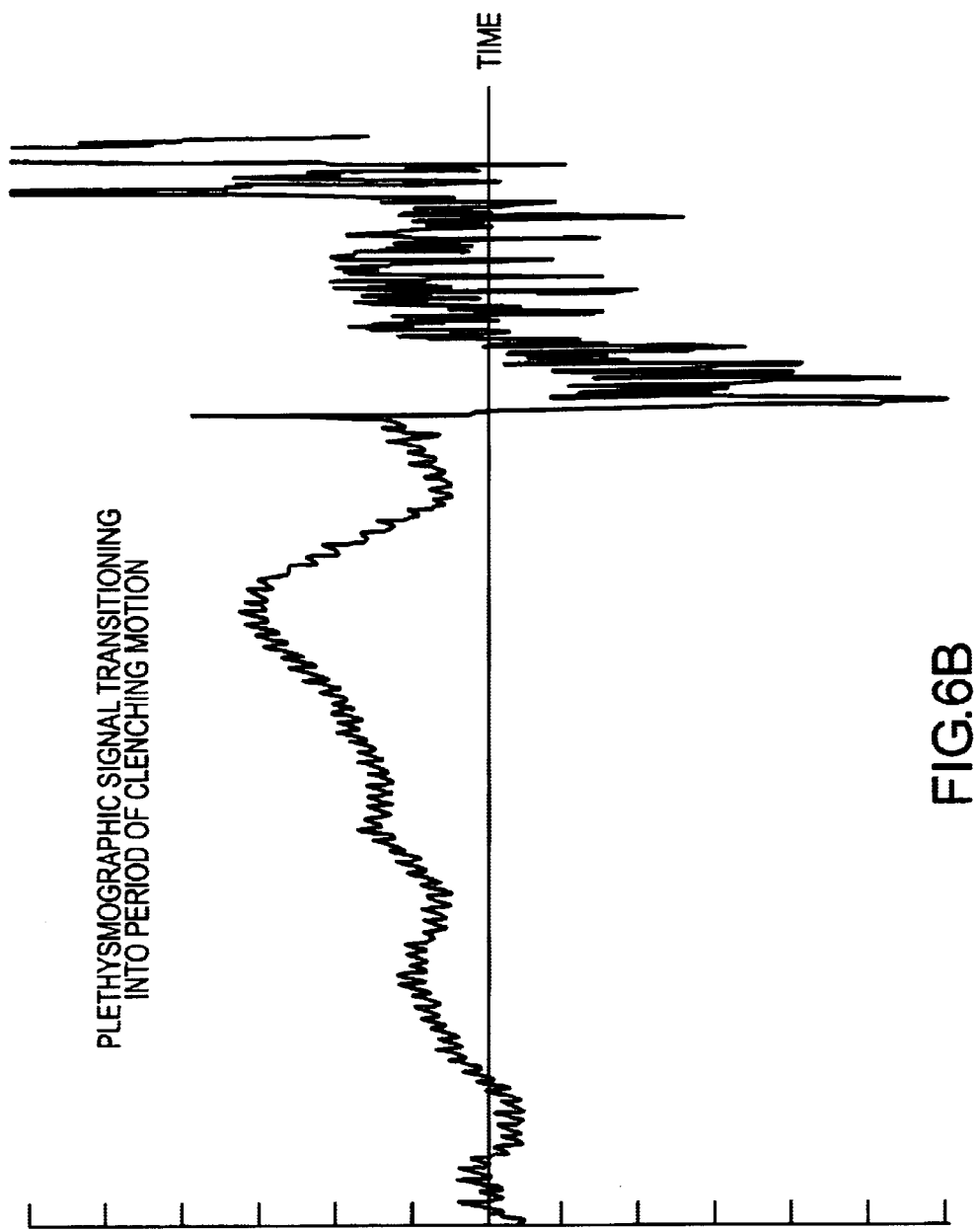
Figure 6D:
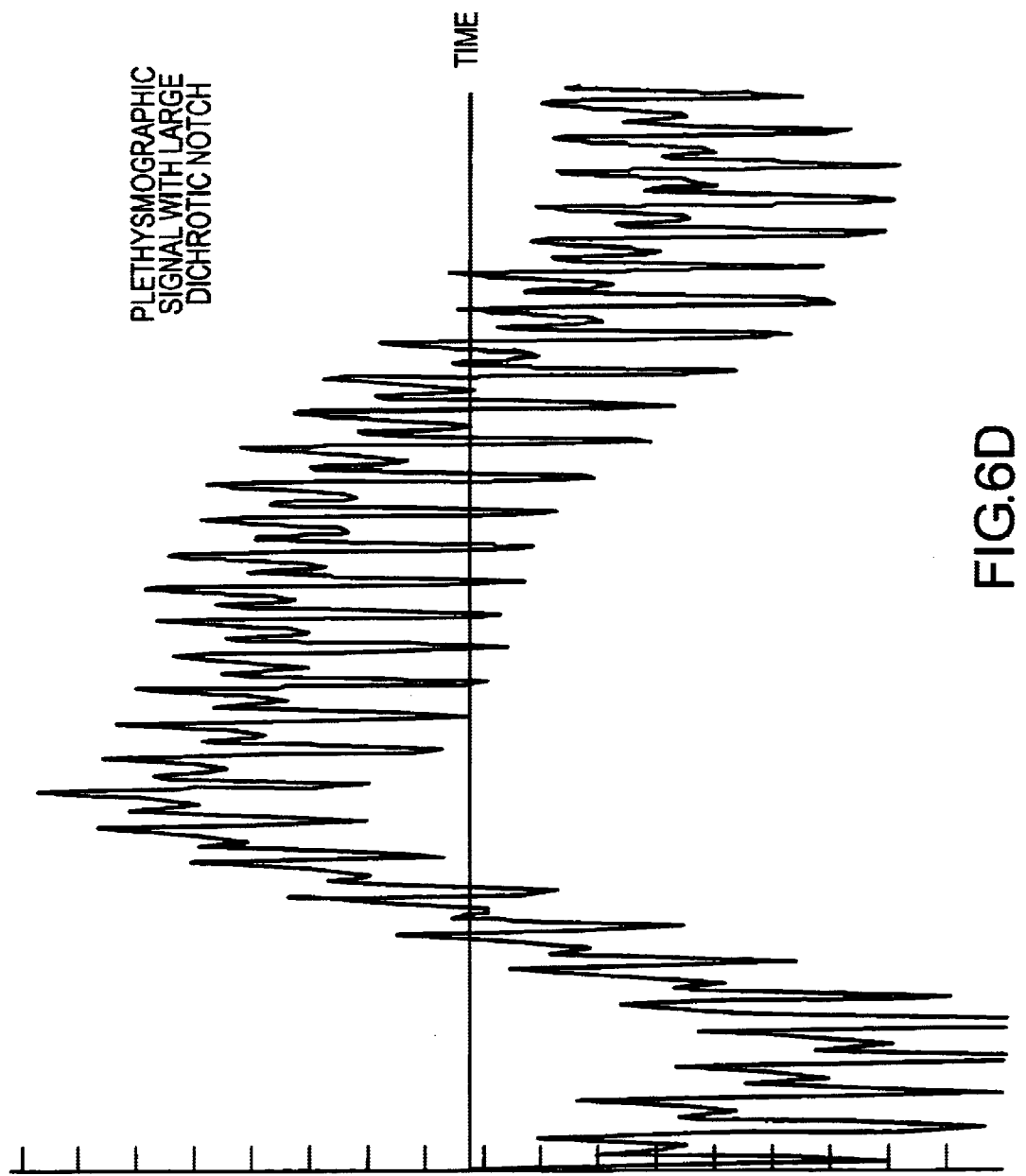

Referring now to FIG. 5, there is shown one embodiment of a method (500) for training the neural network. The neural network training method (500) establishes the appropriate weighting values for the interconnections between the neurons in the neural network architecture. In one embodiment, the neural network training method (500) is implemented on a computer system (e.g., a desktop or laptop computer). After a trained neural network is generated on the computer, the trained neural network can then be installed on a number of pulse oximeters. Although not required, such centralized training of the neural network and installation of the same neural network on multiple pulse oximeters provides for enhanced consistency among the recognition and classification of various plethysmographic signals by different pulse oximeters.

The neural network training method (500) begins with selecting (510) a number of plethysmographic signal data sets that are associated with a number of different types of predetermined signal conditions. The plethysmographic signal data sets may be stored in a database of exemplary plethysmographic signal data sets that is stored on a hard drive of the computer or other storage media accessible by the computer. By way of example, different types of predetermined signal conditions include: (1) normal adult plethysmographic signal; (2) normal baby plethysmographic signal; (3) fixed frequency tapping motion without plethysmographic signal; (4) fixed frequency tapping motion with plethysmographic signal; (5) moving frequency tapping motion without plethysmographic signal; (6) moving frequency tapping motion with plethysmographic signal; (7) clenching motion without plethysmographic signal; (8) clenching motion with plethysmographic signal; (9) baby-kicking motion without plethysmographic signal; (10) baby-kicking motion with plethysmographic signal; (11) irregular plethysmographic signal associated with patient arrhythmia; (12) low perfusion condition plethysmographic signal; (13) plethysmographic signal with fast breathing; (14) plethysmographic signal with shallow breathing; (15) plethysmographic signal with extended breath holding; and (16) no plethysmographic signal. Examples of a number of different red and infrared plethysmographic signal conditions are depicted in FIGS. 6A–D.

Typically, the plethysmographic signal data sets are stored in the form of time domain signals. Thus, the selected plethysmographic signal data sets are transformed (520) from the time domain to the other signal domains (e.g., cepstral, power spectral, bispectral, Wavelet filtered domains) to be utilized as inputs to the neural network processing module (250). Transformation (520) results in a corresponding number of transformed plethysmographic signal data sets. Thereafter, sets or vectors of coefficients are extracted (530) from the transformed plethysmographic signal data sets. As may be appreciated, the steps of transforming (520) and extracting (530) may, for example, be accomplished as described in connection with the transforming step (240) of the method (200) of FIG. 2. In addition to the extracted coefficients, additional signal characteristics may be derived (540) from the plethysmographic signal data sets and the various transformed signal domains. The additional signal characteristics that are derived should be the same ones as are intended to be employed by the neural network processing module (250) in addition to the various signal domain coefficients.

The sets or vectors of extracted coefficients and the additional signal characteristics are then used (550) as inputs to train the neural network. A learning procedure is used to adjust (560) the weighting values associated with the various interconnections between neurons in the neural network until the weighting values are optimized. In this regard, learning procedures such as the backpropagation and simulated annealing may be employed.

In some instances, the trained neural network may have difficultly recognizing and classifying a particular plethysmographic signal encountered in the field. In such instances, it may be desirable to add such plethysmographic signals (e.g., new plethysmographic signals of interest) to the set of training signals used to train a neural network for a new set of pulse oximeters or to retrain the neural network installed in existing pulse oximeters. When encountered in the field, new plethysmographic signals of interest may be stored in the memory device(s) 82 of the pulse oximeter(s) 10. Thereafter, new plethysmographic signals of interest may be retrieved (570) from the memory device(s) 82 of the pulse oximeter(s) and added (580) to the database of plethysmographic signal data sets.

While various embodiments of the present invention have been described in detail, further modifications and adaptations of the invention may occur to those skilled in the art. However, it is to be expressly understood that such modifications and adaptations are within the spirit and scope of the present invention.

What is claimed is:

1. A pulse oximeter comprising:
   a first optical signal source operable to emit an optical signal characterized by a first wavelength;
   a second optical signal source operable to emit an optical signal characterized by a second wavelength different than said first wavelength;
   a detector operable to receive said first and second optical signals after said first and second optical signals are attenuated by a patient tissue site of a patient, said detector being further operable to provide a detector output signal representative of said attenuated first and second optical signals; and
   a processor enabled to obtain first and second time domain plethysmographic signals from the detector output signal and classify at least one of the first and second time domain plethysmographic signals using a neural network, said neural network receiving input coefficients derived from at least one transform of said at least one of said first and second time domain plethysmographic signals.

2. The pulse oximeter of claim 1 wherein said at least one of said first and second time domain plethysmographic signals is classified by said neural network as being associated with at least one of a plurality of different types of predetermined signal conditions.

3. The pulse oximeter of claim 2 wherein the plurality of different types of predetermined signal conditions comprise:
   (1) Normal adult plethysmographic signal;
   (2) Normal baby plethysmographic signal;
   (3) Fixed frequency tapping motion without plethysmographic signal;
   (4) Fixed frequency tapping motion with plethysmographic signal;
   (5) Moving frequency tapping motion without plethysmographic signal;
   (6) Moving frequency tapping motion with plethysmographic signal;
   (7) Clenching motion without plethysmographic signal;
   (8) Clenching motion with plethysmographic signal;
   (9) Baby-kicking motion without plethysmographic signal;
   (10) Baby-kicking motion with plethysmographic signal;
   (11) Irregular plethysmographic signal associated with patient arrhythmia;
   (12) Low perfusion condition plethysmographic signal;
   (13) Plethysmographic signal with fast breathing;
   (14) Plethysmographic signal with shallow breathing;
   (15) Plethysmographic signal with extended breath holding; and
   (16) No plethysmographic signal.

4. The pulse oximeter of claim 2 wherein said neural network is trained prior to field use with data sets representative of each of said plurality of different types of predetermined signal conditions.

5. The pulse oximeter of claim 4 wherein said neural network comprises a fuzzy neural network that has been trained prior to field use in a manner achieving fuzzification of said pre-trained neural network.

6. The pulse oximeter of claim 1 wherein said at least one transform comprises at least one of a spectral transform, a bispectral transform, a cepstral transform, and Wavelet filter bank transform.

7. The pulse oximeter of claim 6 wherein, in addition to said coefficients, said neural network further receives at least one signal characteristic derived from at least one of the first time domain plethysmographic signal, the second time domain plethysmographic signal, and said at least one transform of said at least one of said first and second time domain plethysmographic signals.

8. The pulse oximeter of claim 7 wherein said at least one signal characteristic comprises at least one of:
   (1) An RMS energy measure;
   (2) A spikiness measure;
   (3) A spectral jitter measure;
   (4) A spectral shimmer measure;
   (5) A spectral smear measure;
   (6) A cepstral peak jitter measure; and
   (7) A cepstral peak position measure.

9. The pulse oximeter of claim 1 wherein said neural network comprises one of a feed-forward network and a recursive network.

10. The pulse oximeter of claim 9 wherein inputs to an intermediate layer of said neural network are used to fuzzify the input coefficients to an initial layer of said neural network.

11. The pulse oximeter of claim 1 wherein said first wavelength is within the range of infrared light wavelengths and said second wavelength is within the range of red light wavelengths.

12. The pulse oximeter of claim 1 wherein said pulse oximeter further comprises:
   a drive system operable to cause operation of said first and second optical signal sources such that each of said first and second optical signal sources emit first and second optical signals, respectively, in accordance with a multiplexing method;

a sampler operable to sample the detector output signal at a desired sampling rate and output a signal having a series of sample values representative of said attenuated first and second optical signals; and wherein said processor comprises a digital processor, said digital processor being further operable to demultiplex the series of sample values to obtain said first and second time domain plethysmographic signals.

13. The pulse oximeter of claim 12 wherein said desired sampling rate is at least 50 Hz.

14. The pulse oximeter of claim 12 wherein said multiplexing method comprises at least one of frequency division multiplexing, time division multiplexing, and code division multiplexing.

15. A method of processing a plethysmographic signal obtained from a patient, the plethysmographic signal being obtained in a first signal domain, said method comprising the steps of:

transforming the plethysmographic signal from the first domain to a plurality of signal domains different from the first domain to obtain a corresponding plurality of transformed plethysmographic signals, each transformed plethysmographic signal being in one of the different signal domains;

selecting a plurality of sets of coefficients, each set of coefficients being derived from a corresponding one of the transformed plethysmographic signals;

inputting the sets of coefficients to a neural network; and classifying the plethysmographic signal based on an output from the neural network.

16. The method of claim 15 wherein the first domain comprises the time domain and wherein said step of transforming comprises:

transforming the plethysmographic signal from the time domain to the spectral domain to obtain a spectral domain plethysmographic signal; and transforming the spectral domain plethysmographic signal to the cepstral domain to obtain a cepstral domain plethysmographic signal.

17. The method of claim 16 wherein said step of transforming the plethysmographic signal from the time domain to the spectral domain comprises:

performing a Fourier transformation on the time domain plethysmographic signal.

18. The method of claim 16 wherein said step of transforming the plethysmographic signal from the spectral domain to the cepstral domain comprises:

performing a Fourier transformation on the spectral domain plethysmographic signal.

19. The method of claim 16 wherein said step of transforming further comprises:

transforming the plethysmographic signal from the time domain to the bispectral domain to obtain a bispectral domain plethysmographic signal.

20. The method of claim 19 wherein said step of transforming the plethysmographic signal from the time domain to the bispectral domain is performed in accordance with the following expression:

$$B(\omega_1,\omega_2)=E[F(\omega_1)F(\omega_2)\overline{F(\omega_1+\omega_2)}]$$

where $\omega_1$ and $\omega_2$ are the frequencies present in spectrums of the time domain plethysmographic signal.

21. The method of claim 16 wherein said step of transforming further comprises:

applying a Wavelet filter bank transform to the time domain plethysmographic signal to obtain a Wavelet filtered domain plethysmographic signal.

22. The method of claim 15 further comprising:

deriving at least one signal characteristic using information included in at least one of the first domain plethysmographic signal or the transformed plethysmographic signals; and inputting the at least one signal characteristic to the neural network in addition to the sets of coefficients.

23. The method of claim 22 wherein, in said step of deriving, the at least one signal characteristic comprises at least one of:

(1) An RMS energy measure;

(2) A spikiness measure;

(3) A spectral jitter measure;

(4) A spectral shimmer measure;

(5) A spectral smear measure;

(6) A cepstral peak jitter measure; and (7) A cepstral peak position measure.

24. The method of claim 15 wherein, in said step of selecting, each set of coefficients corresponds with a plurality of frames of its corresponding transformed plethysmographic signal.

25. The method of claim 15 wherein said step of classifying comprises:

associating the output from the neural network with at least one of a plurality of different types of predetermined signal conditions.

26. The method of claim 25 wherein, in said step of associating, the plurality of different types of predetermined signal conditions comprise:

(1) Normal adult plethysmographic signal;

(2) Normal baby plethysmographic signal;

(3) Fixed frequency tapping motion without plethysmographic signal;

(4) Fixed frequency tapping motion with plethysmographic signal;

(5) Moving frequency tapping motion without plethysmographic signal;

(6) Moving frequency tapping motion with plethysmographic signal;

(7) Clenching motion without plethysmographic signal;

(8) Clenching motion with plethysmographic signal;

(9) Baby-kicking motion without plethysmographic signal;

(10) Baby-kicking motion with plethysmographic signal;

(11) Irregular plethysmographic signal associated with patient arrhythmia;

(12) Low perfusion condition plethysmographic signal;

(13) Plethysmographic signal with fast breathing;

(14) Plethysmographic signal with shallow breathing;

(15) Plethysmographic signal with extended breath holding; and

(16) No plethysmographic signal.

27. The method of claim 25 further comprising:

training the neural network prior to field use with data sets representative of each of said plurality of different types of predetermined signal conditions.

28. The method of claim 27 wherein, in said step of training, the neural network is trained prior to field use in a manner achieving fuzzification of the neural network.

29. The method of claim 27 wherein, in said step of training, the neural network is trained in accordance with one of a backpropagation learning procedure and a simulated annealing learning procedure.

30. The method of claim 29 wherein, in said step of training, the backpropagation learning procedure is implemented with fuzzy logic control.

31. The method of claim 15 further comprising:
transmitting an optical signal through a tissue site of the patient to obtain the first domain plethysmographic signal.

32. A method of training a neural network to classify a plethysmographic signal obtained from a patient, said method comprising the steps of:
selecting a plurality of first domain plethysmographic signal data sets associated with a plurality of different types of predetermined signal conditions from a database of plethysmographic signal data sets;
transforming the first domain plethysmographic signal data sets to other signal domains different than the first domain to obtain a corresponding plurality of transformed plethysmographic signal data sets;
extracting a plurality of sets of coefficients from the transformed plethysmographic signal data sets, each set of coefficients being extracted from a corresponding one of the transformed plethysmographic signal data sets;
using the sets of extracted coefficients as inputs to the neural network; and
adjusting weighting values associated with connections between neurons in the neural network in accordance with a learning procedure.

33. The method of claim 32 wherein, in said step of selecting, the plurality of different types of predetermined signal conditions comprise:
(1) Normal adult plethysmographic signal;
(2) Normal baby plethysmographic signal;
(3) Fixed frequency tapping motion without plethysmographic signal;
(4) Fixed frequency tapping motion with plethysmographic signal;
(5) Moving frequency tapping motion without plethysmographic signal;
(6) Moving frequency tapping motion with plethysmographic signal;
(7) Clenching motion without plethysmographic signal;
(8) Clenching motion with plethysmographic signal;
(9) Baby-kicking motion without plethysmographic signal;
(10) Baby-kicking motion with plethysmographic signal;
(11) Irregular plethysmographic signal associated with patient arrhythmia;
(12) Low perfusion condition plethysmographic signal;
(13) Plethysmographic signal with fast breathing;
(14) Plethysmographic signal with shallow breathing;
(15) Plethysmographic signal with extended breath holding; and
(16) No plethysmographic signal.

34. The method of claim 32 wherein, in said step of transforming the first domain plethysmographic signal data sets to other signal domains, the signal domains different than the first domain comprise spectral, cepstral, bispectral and Wavelet filter bank signal domains.

35. The method of claim 32 wherein, in said step of adjusting, the weighting values are adjusted in accordance with one of a backpropagation learning procedure and a simulated annealing learning procedure.

36. The method of claim 32 further comprising:
deriving at least one signal characteristic using information included in at least one of the first domain plethysmographic signal data sets and the transformed plethysmographic signal data sets; and
using the at least one signal characteristic as an input to the neural network in addition to the extracted coefficients.

37. The method of claim 36 wherein, in said step of deriving, the at least one signal characteristic comprises at least one of:
(1) An RMS energy measure;
(2) A spikiness measure;
(3) A spectral jitter measure;
(4) A spectral shimmer measure;
(5) A spectral smear measure;
(6) A cepstral peak jitter measure; and
(7) A cepstral peak position measure.

38. The method of claim 32 further comprising:
storing plethysmographic signals of interest.

39. The method of claim 38 wherein, in said step of storing, the plethysmographic signal of interest is stored in a memory device of a pulse oximeter.

40. The method of claim 38 further comprising:
retrieving the stored plethysmographic signal of interest; and
adding the plethysmographic signal of interest to the database of plethysmographic signal data sets.

41. A method of providing information relating to a physiological condition of a patient based on at least one plethysmographic signal obtained from the patient, the plethysmographic signal being obtained in a first signal domain, said method comprising the steps of:
transforming the plethysmographic signal from the first domain to a plurality of signal domains different from the first domain to obtain a corresponding plurality of transformed plethysmographic signals, each transformed plethysmographic signal being in one of the different signal domains;
classifying the plethysmographic signal based on an output from a neural network, wherein the output of the neural network is based on input coefficients derived from at least one of the transformed plethysmographic signals; and
selecting a technique for determining the physiological condition of the patient based on the classification.

42. The method of claim 41 wherein the physiological condition of the patient comprises a pulse rate.

43. The method of claim 41 wherein at least two plethysmographic signals corresponding to different optical wavelengths are transformed and classified, and wherein the physiological condition of the patient comprises an SpO2 value.

44. The method of claim 41 wherein at least two plethysmographic signals corresponding to different optical wavelengths are transformed and classified, the plethysmographic signals being transformed using at least a Wavelet filter bank transform, and wherein the physiological condition of the patient comprises a respiration index.

45. The method of claim 41 wherein the first domain comprise the time domain and the plurality of signal domains different than the first domain comprise spectral, cepstral, bispectral and Wavelet filtered domains.

* * * * *